United States Patent

Franceschi et al.

[11] Patent Number: 5,941,390
[45] Date of Patent: Aug. 24, 1999

[54] PACKAGE FOR FOLDING INTRAOCULAR IMPLANTS

[75] Inventors: François Franceschi, Marseille; Aldo Duchesne, St Jorioz; Dominique Durand, Annecy, all of France

[73] Assignee: Corneal Laboratoires, Paris, France

[21] Appl. No.: 09/171,060

[22] PCT Filed: Apr. 22, 1997

[86] PCT No.: PCT/FR97/00717

§ 371 Date: Oct. 9, 1998

§ 102(e) Date: Oct. 9, 1998

[87] PCT Pub. No.: WO97/39701

PCT Pub. Date: Oct. 30, 1997

[30] Foreign Application Priority Data

Apr. 22, 1996 [FR] France ................................. 96/05004

[51] Int. Cl.⁶ .................................................. A61B 17/00
[52] U.S. Cl. ........................................ 206/438; 606/107
[58] Field of Search .................................. 206/363, 370, 206/438, 454; 606/107

[56] References Cited

U.S. PATENT DOCUMENTS

| | | |
|---|---|---|
| 4,844,093 | 7/1989 | Jampel et al. . |
| 4,906,247 | 3/1990 | Fritch . |
| 4,911,158 | 3/1990 | Weatherly . |
| 5,139,501 | 8/1992 | Klass . |
| 5,190,553 | 3/1993 | Kanert et al. . |
| 5,201,763 | 4/1993 | Brady et al. . |
| 5,556,400 | 9/1996 | Tunis .................................. 606/107 |
| 5,578,042 | 11/1996 | Cumming ............................ 606/107 |
| 5,615,770 | 4/1997 | Applebaum et al. ................ 206/438 |

FOREIGN PATENT DOCUMENTS

| | | |
|---|---|---|
| 0 503 136 | 9/1992 | European Pat. Off. . |
| 2 673 526 | 9/1992 | France . |
| 40 39 119 | 9/1991 | Germany . |

Primary Examiner—Jacob K. Ackun
Attorney, Agent, or Firm—Wolf, Greenfield & Sacks P.C.

[57] ABSTRACT

The invention relates to packaging for folding intraocular implants having a flexible optical portion. The packaging (70) comprises: a base (31); folding support means (30) for supporting the optical portion (24) and comprising a folding edge (34) substantially parallel to said base, which edge is suitable for coming into contact with a portion of the bottom face of the optical portion (24) and forms a longitudinal axis (32) enabling the implant to be folded along said folding axis (28) on either side of said folding edge (34); and positioning means (50; 56; 60) designed to co-operate with at least a portion of the peripheral zone (26) of the optical portion (24) to support the implant and to enable the folding axis (28) of the implant to be maintained in the same vertical plane as the longitudinal axis (32) of said fold support means (30).

10 Claims, 4 Drawing Sheets

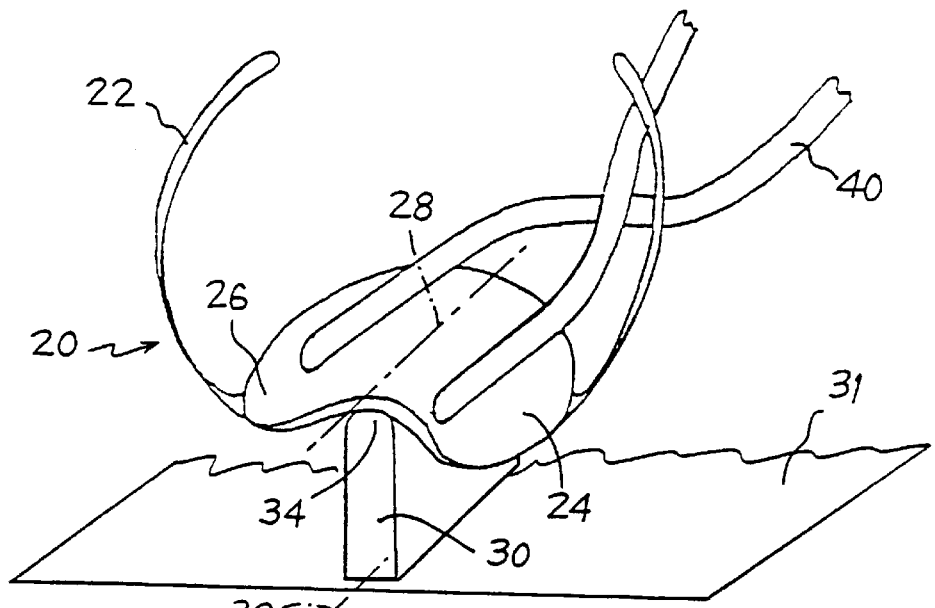
FIG_1
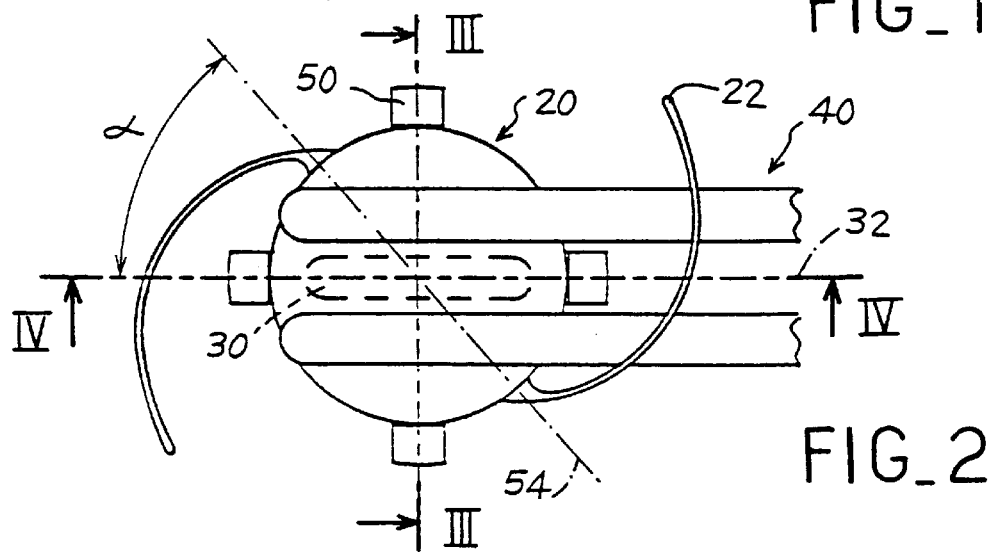
FIG_2
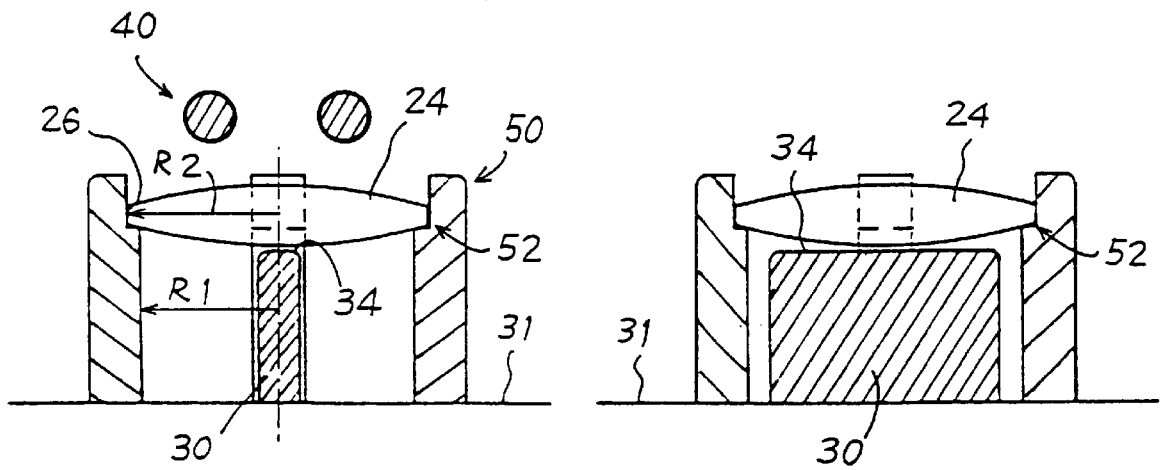
FIG_3  FIG_4

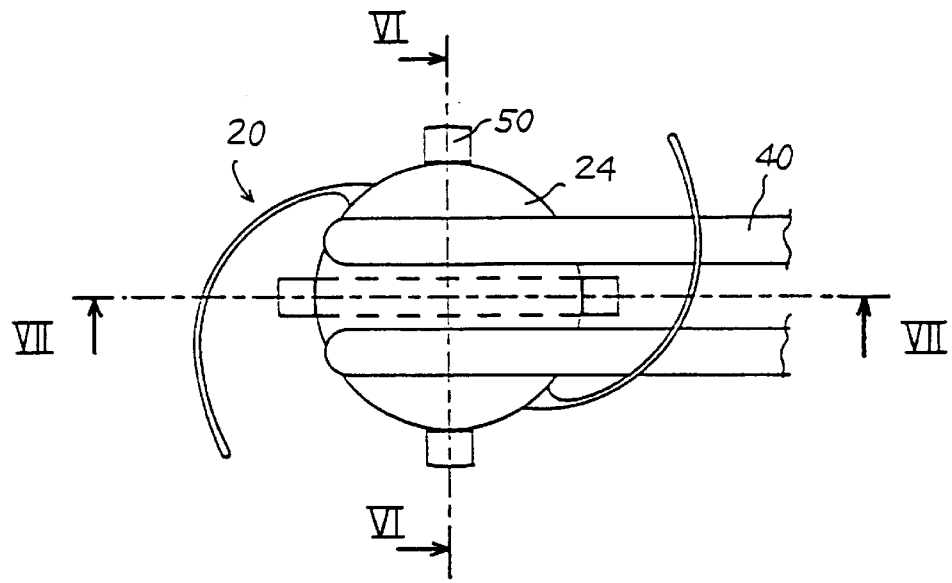
FIG_5
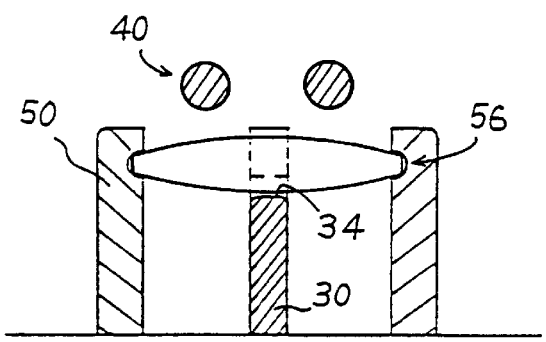 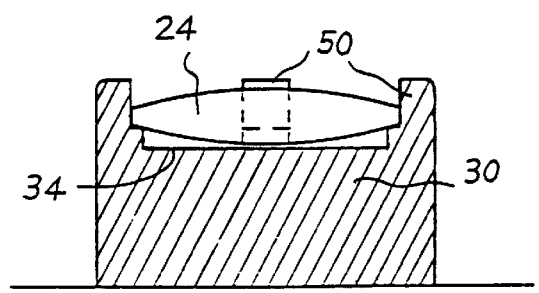
FIG_6  FIG_7

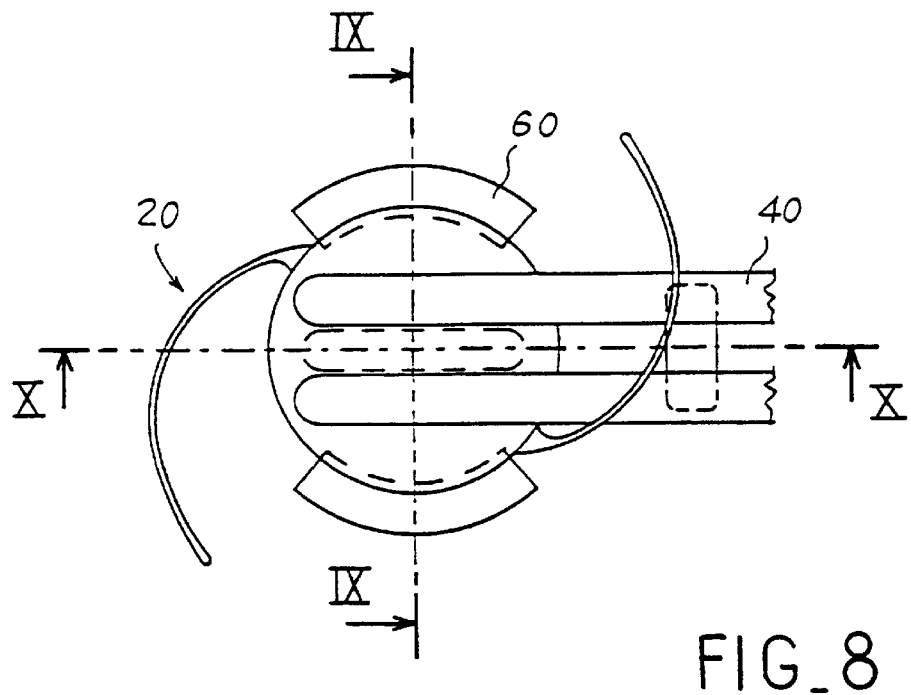
FIG_8
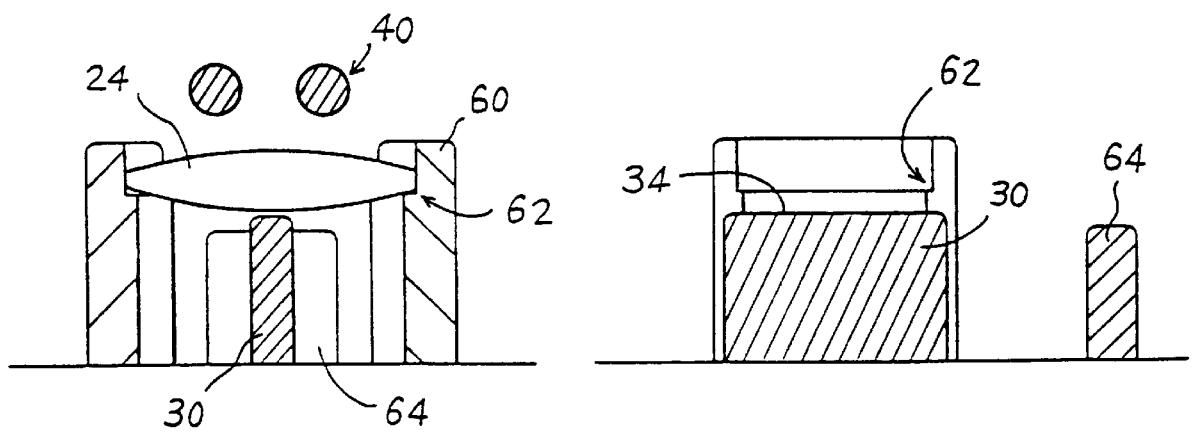
FIG_9  FIG_10

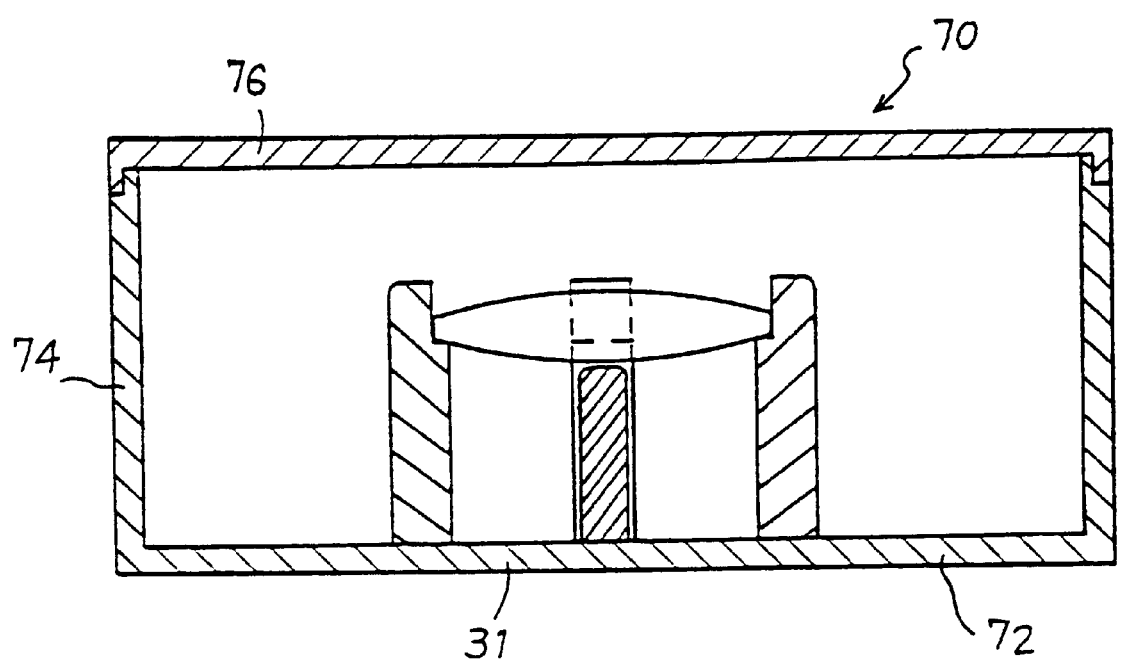
FIG_11

PACKAGE FOR FOLDING INTRAOCULAR IMPLANTS

The present invention relates to packaging including a device for folding intraocular implants made up of a haptic portion and of a flexible optical or lens portion and having a folding axis.

An intraocular implant constitutes an optical system for correcting the vision of the human eye and can, in some cases, be used instead of contact lenses or external correcting glasses. An intraocular implant essentially comprises an optical portion of generally circular or slightly oval shape constituting the correcting optical system proper, and a haptic portion which serves for placing the optical portion inside the eye, for fixing it, and for holding it in the correct position.

New operative techniques make it possible to reduce the size of the incision made in the eye. Thus, with a cataract operation, the "phaco-emulsification" operative technique makes possible the ablation of the opaque crystalline lens of the eye by inserting into the eye an ultrasonic probe having an irrigation/suction system. Under the combined action of ultrasonics and the flow of a balanced saline solution, the lens is removed by emulsification.

Especially compared with prior techniques, that operative technique presents the particular advantage of requiring only a small incision to be made in the cornea, using a knife pre-calibrated to 3.2 mm, to enable the instruments required for such ablation to be inserted into the eye. It will be understood that under such circumstances it is advantageous to have implants that can be inserted into the eye via the incision that is made for the phaco-emulsification operation, i.e. via an incision that is about 3 mm to 4 mm long.

That is why new, "flexible", intraocular implants have been developed. Such an implant has an optical portion made out of a flexible material which enables the optical portion to be folded before the implant is inserted into the eye via the incision, with the optical portion returning to its initial shape after it has been placed in the eye. At present, two major types of substance are used for making flexible optics. These substances are generally referred to by their generic names, being firstly flexible acrylics such as PHEMA, and secondly polysiloxane gel. These materials have the required optical properties and they are also biocompatible.

When an intraocular implant having a flexible optic is being placed, one of the crucial points is actually folding the implant, since this step requires great accuracy and a high degree of dexterity on the part of the practitioner, firstly to obtain a folded implant that is of as small a width as possible, and secondly to keep the implant folded without it escaping or being damaged. It will be understood that choosing the zones via which the implant is held in the folded state is fundamental in satisfying the above-mentioned conditions.

At present, there exist several techniques for folding implants and placing them, all of which techniques attempt to solve those problems. A first solution consists in using an implant which has previously been folded and which is held in the folded state in its package. That solution is unsatisfactory since the length of time the implant is stored prior to use can be as long as five years, and it is highly probable that the implant will have suffered deformation including a residual component which would be catastrophic in terms of varying the optical characteristics of the implant; in addition, the problem of gripping the implant prior to inserting it into the eye remains unsolved.

Another solution consists in placing the folded implant in a pipe and in guiding the implant into the eye by pushing it. Under such circumstances, the implant is subjected to numerous mechanical stresses and it is difficult to control its placement within the eye.

The solution presently in most widespread use employs a pair of forceps: a first forceps that is simple, having parallel arms for holding the implant along a diameter of its optical portion, which diameter is selected to be as close as possible to the folding axis that makes it possible to obtain the smallest possible width of folded implant; and a second forceps that has crossed jaws, making it possible firstly to initiate curving of the optical portion, and subsequently to fold it symmetrically prior to holding the folded implant on its own. That technique requires perfect coordination between both hands while they perform opposite movements, given the different types of forceps being used, and it also requires each pair of forceps to be perfectly positioned. The position of the simple forceps determines the folding axis of the implant and thus its width when in the folded position, while the position of the crossed-jaw forceps, at the moment when its jaws are holding the implant tightly enough to retain it without help from the first forceps, determines whether a good hold is obtained on the implant, and thus whether the implant is easy to place in the eye.

An object of the invention is to provide packaging including a device for folding an intraocular implant made up of a flexible optical portion and of a haptic portion, the device making it possible to fold the implant in a manner that is simple and reliable prior to the implant being placed in the eye, so that the implant can be folded, taken hold of, and placed quickly and accurately.

To achieve this object, the folding device of the invention for folding intraocular implants is characterized in that it comprises:

a base;

folding support means secured to said base for the purpose of supporting folding of the optical portion, said means possessing a longitudinal rib having a folding edge substantially parallel to said base and suitable for coming into contact with a portion of the bottom face of the optical portion, and forming a longitudinal axis designed to be placed in the same vertical plane as the folding axis of the implant so as to enable the implant to be folded along said folding axis on either side of said folding edge; and positioning means secured to said base and designed to co-operate with at least a portion of the peripheral zone of the optical portion of the implant to support the implant, said positioning means enabling the folding axis of the implant to be maintained in the same vertical plane as the longitudinal axis of said folding support means;

and in that said base of the folding device carries and interconnects the folding support means and the positioning means, and also constitutes the bottom of the packaging.

It will be understood that this device makes it easier to fold the implant, to take hold of the folded implant, and then subsequently to place the implant in the eye. The surgeon needs only one forceps as the folding tool, with the implant bearing, during the folding operation, against the folding support means which can be in the form of a longitudinal rib.

On its own, the device of the invention does not make it possible to fold the optical portion of the implant, but it does make folding easy and simple to perform while using only a single forceps.

In an advantageous configuration, the positioning means are shaped so as to maintain the mean plane of the optical portion of the implant temporarily perpendicular to the vertical plane containing the folding axis and the folding edge. In this case, the mean plane of the optical portion can be defined as the plane of intersection between the two spherical caps making up the two convex faces of the optical portion.

According to another advantageous characteristic, the positioning means comprise radial retaining means for retaining at least a portion of the edge of the optical portion of the implant to be folded, and designed to place the optical center of the implant on the longitudinal axis of the folding support means and to prevent any relative rotation between the implant and said folding device. This characteristic makes it possible to maintain the folding axis of the implant in the same vertical plane as the longitudinal axis of the rib so that folding does not take place along some other diameter of the implant, i.e. after the implant has rotated relative to the rib.

Preferably, reference points are provided enabling the implant to be positioned accurately relative to the folding device. The surgeon then needs to concentrate solely on manipulating the single forceps in order to obtain a good hold on the folded implant by selecting a correct position for the forceps, i.e. a distance between the forceps and the folding axis that is sufficient to enable the folded implant to be held but that is not too great so as to avoid the implant slipping out of the forceps.

Provision is also made for the device of the invention further to include abutment means for limiting the vertical stroke of the folding tool, i.e. the forceps, in a position that is suitable for holding the folded implant.

The invention also provides packaging for an intraocular implant including the folding device of the invention in which the base of the folding device constitutes the bottom of the box of the packaging in which the implant is placed while it is being packaged.

It will be understood that by means of these advantageous characteristics the device of the invention provides optimum folding and gripping of the implant by the surgeon prior to placing the implant in the eye since all of the geometrical parameters of the successive positions taken up by the forceps relative to the implant during the folding operation are determined by the shape of the device of the invention.

The invention will be better understood and secondary characteristics and advantages thereof will appear on reading the description of embodiments given below by way of example.

It should be understood that the description and the drawings are given solely by way of non-limiting indication.

Reference is made to the accompanying drawings, in which:

FIG. 1 is a diagrammatic perspective view showing the principle whereby a flexible-optics intraocular implant is folded using the device of the invention;

FIG. 2 is a plan view of the device of the invention with the folding tool and the intraocular implant in the position preceding the folding operation;

FIG. 3 is a cross-section on III—III of FIG. 2;

FIG. 4 is an axial section on IV—IV of FIG. 2 in which, for greater clarity, the folding tool is not shown;

FIG. 5 is a view identical to that of FIG. 2 showing a variant embodiment of the device of the invention;

FIG. 6 is a cross-section on VI—VI of FIG. 5;

FIG. 7 is an axial section on VII—VII of FIG. 5 in which, for greater clarity, the folding tool is not shown;

FIG. 8 is a view identical to that of FIG. 2 for another variant embodiment of the device of the invention;

FIG. 9 is a cross-section on IX—IX of FIG. 8;

FIG. 10 is an axial section on X—X of FIG. 8, in which, for greater clarity, the folding tool and the implant are not shown; and FIG. 11 is a diagrammatic vertical section through a packaging box incorporating the device for folding implants.

The device of the invention is usable with an intraocular implant 20 comprising an optical portion 24 which is necessarily flexible, and a haptic portion 22 which, by way of non-exclusive example, may be in the form of two symmetrical loops. The loops are connected to the periphery or edge 26 of the optical portion 24. One of the diameters of the optical portion forms a preferred folding axis 28 which gives rise to a folded implant having the smallest possible width.

As can be seen in FIG. 1, the principle of the device of the invention consists in support means, such as a longitudinal rib 30 projecting from a base 31, for use in folding the optical portion. The support means form a longitudinal axis 32 that is to be placed in the same vertical plane as the folding axis 28 of the implant 20 so that the implant 20 can be folded along the folding axis 28 on either side of the rib 30 by using a folding tool such as a forceps 40.

FIGS. 2 to 4 show a device for folding intraocular implants in co-operation with the forceps 40, together with the intraocular implant 20 in the position prior to the folding operation.

The folding device comprises the longitudinal rib 30 of axis 32 and four identical point supports 50 that are spaced circumferentially outside an imaginary circle around the rib 30, the center of the circle lying on the same vertical as the geometrical center of the rib 30. The rib and the supports preferably do not have any sharp angles so as to avoid damaging the optical portion of the implant, and they project at right angles from the base 30 which carries them and interconnects them.

Preferably, the main direction of the section of the rib 30 is perpendicular to the plane of the base 31, with the length of the rib occupying at least a substantial fraction of the diameter of the optical portion of the implant (the rib may be a little longer or a little shorter than the diameter of the optical portion), the width of the rib is about 1 mm so as to be wide enough to curve the optical portion without damaging it while also being narrow enough to enable the optical portion to be folded in half far enough to enable the folded implant to be held between the two jaws of the forceps, and the top or folding edge of the rib is rounded.

The supports 50 are placed on the base 31 at 90° intervals from one another and each has a shoulder 52 on the radially internal side of the imaginary circle with the radius of the circle increasing from a value R1 to a value R2>R1 at the shoulder 52 on going up from the lower portion of the support 50 towards its upper portion.

The radius R2 is the same order of magnitude as the radius of the optical portion 24 of the implant such that the edge 26 of the implant rests on the shoulders 52.

The shoulders 52 make it possible firstly to hold the implant horizontally, i.e. substantially parallel to the base 31, and secondly to center the optical portion of the implant on the folding edge 34 of the rib. Prior to folding, the mean plane of the optical portion of the implant is thus temporarily perpendicular to the vertical plane containing the folding axis 28 of the implant and the folding edge 34 of the rib.

The vertical wall of each shoulder 52 is preferably placed on the imaginary circle of radius R2, where R2 is slightly smaller than the diameter of the optical portion of the implant so as to hold the implant securely in a radial direction prior to folding, and the width of the shoulder is small so as to enable the edge 26 of the optical portion to escape or to separate from the supports 50 while folding is taking place. In this way, the vertical wall of the shoulders 52 retains the periphery of the optical portion of the implant by friction contact, thereby preventing any rotary movement between the implant and the folding device and making it possible, up to the moment of folding, to retain the configuration in which the preferred folding axis of the implant coincides with the longitudinal axis 32 or edge of the rib.

The height between the imaginary circle and the top of the rib is not less than half the thickness of the optical portion at its center.

During packaging of the implant in a package containing the device of the invention, or while preparing the operation of placing the implant in the eye of a patient, the implant needs to be correctly positioned on the device. Reference points (not shown) are preferably present on the bottom of the device to show the relative position between the implant and the folding device in which the longitudinal axis 32 of the rib 30 and the optimum folding axis 48 of the implant are superposed. In this configuration, the axis 32 of the rib and the axis 54 corresponding to the diameter of the optical portion passing through the middle of the base of each of the two loops form an angle $\alpha=45°$, approximately.

Immediately before the folding operation proper, the two parallel jaws of the forceps 40 are positioned on either side of the rib 30 over the implant 20. It then suffices to lower the forceps in downward vertical translation to fold the implant, i.e. the optical portion is curved diametrically along the folding axis 28 with its edge 26 then escaping from the shoulders 52 of the supports 50. Thereafter the two jaws should be moved towards each other a little to wedge the implant between the jaws of the forceps, and finally it remains only to separate the implant from the device using the forceps which hold the implant reliably for placing it in the eye of the patient in the ordinary way.

In FIGS. 5 to 10, the same numerical references are used again to designate elements identical to elements in FIGS. 2 to 4.

The embodiment of the device of the invention shown in FIGS. 5 to 7 differs in that two of the supports 50 lie on the longitudinal axis 32 of the rib 30 and physically extend said rib, and in that the other two supports 50, instead of having shoulders 52, have respective notches 56 shaped to receive the edge 26 of the optical portion of the implant. This configuration still enables the forceps 40 to pass on either side of the rib 30 to fold the implant 20 along its folding axis 28. The notches 56 hold the implant more reliably in position relative to the device so that it has the smallest possible width once it has been folded.

The notches 56 form means for retaining at least a portion of the edge 26 of the optical portion of the implant that is to be folded. The notches 56 perform the same functions as the shoulders as described above and also serve to hold the implant vertically by preventing the edge of the optical portion of the implant from moving away from the base 31. Such notches make it possible to transport the implant on its folding device without modifying the prepositioning performed while the implant is being placed on said device.

The other variant embodiment of the device of the invention, as shown in FIGS. 8 to 10, consists firstly in at least some of the positioning means having an outline in a horizontal plane which is substantially identical to the outline of the corresponding zone of the periphery of the optical portion of the implant to be folded, and secondly in that the device further includes abutment means for limiting the vertical stroke of the folding tool (the forceps) in a position suitable for holding the folded implant.

In vertical section, the two supports 60 are identical to the supports 50: a shoulder 62 serves to support the edge of the optical portion of the implant. These supports 60 are disposed symmetrically about the longitudinal axis of the rib, and in a horizontal plane their outline is in the form of an arc of a circle so as to follow the outline of the optical portion of the implant. Like the supports 50, the supports 60 enable the edge of the optical portion to be held prior to folding and they enable the optical portion to be released when folding is taking place.

This variant embodiment also includes a vertical abutment 64 projecting from the base 31 to limit the stroke of the forceps 40 when the implant is being folded. The abutment 64 is placed in alignment with the rib 30, and it is both wider and lower than the rib 30, so as to limit the stroke of the forceps 40 to a height that is suitable for enabling the forceps to hold the implant properly when pressed against the folded optical portion. Thereafter, it suffices to disengage the implant from the folding device.

FIG. 11 is a diagram showing a preferred embodiment of the invention in which the above-described device is incorporated in a packaging box 70 having a bottom 72 constituted by the base 31 of the device for folding implants. To form the box, the bottom is extended by vertical walls 74 and by a removable lid 76.

It will be understood that in the invention all of the elements constituting the folding device are fixed to the base 31 and that they are stationary, i.e. they are incapable of movement or displacement, even of relative movement or displacement, in particular between the positioning means and the folding support means.

Other modifications can be applied to the device described without going beyond the ambit of the invention. For example, it is possible to provide some other number of point supports, there being at least three of them, or the top face of the rib can be cup-shaped and also serve as a zone for supporting a portion of the central zone of the optical portion of the implant. The use of at least one notch in the positioning means makes it possible to hold the implant more reliably in a packaging box 70. In the invention, the height of the rib 30 is at least approximately half the diameter of the optical portion of the implant.

We claim:

1. Packaging including a device for folding intraocular implants comprising a flexible optical portion and a haptic portion and having a fold axis wherein said device comprises:

a base;

folding support means secured to said base for the purpose of supporting folding of the optical portion, said means possessing a longitudinal rib having a folding edge substantially parallel to said base and suitable for coming into contact with a portion of the bottom face of the optical portion, and forming a longitudinal axis designed to be placed in the same vertical plane as the folding axis of the implant so as to enable the implant to be folded along said folding axis on either side of said folding edge; and positioning means secured to said base and designed to co-operate with at least a portion of the peripheral zone of the optical portion of the implant to support the implant, said positioning means enabling the folding axis of the implant to be maintained in the same vertical plane as the longitudinal axis of said folding support means;

said base of the device carrying and interconnecting the folding support means and the positioning means, and also constituting the bottom of the packaging which is extended by vertical walls and by a lid.

2. Packaging for folding intraocular implants according to claim 1, wherein the positioning means lie on a plane perpendicular to a vertical plane containing the fold axis and the folding edge so as to temporarily maintain a mean plane of the optical portion of the implant, perpendicular to said vertical plane containing the fold axis and the folding edge, the mean plane being a plane of intersection between two spherical caps forming two faces of the optical portion.

3. Packaging for folding intraocular implants according to claim 2, wherein the positioning means comprise radial retaining means for retaining at least a portion of the edge of the optical portion of the implant to be folded, and designed to place an optical center of the implant on the longitudinal axis of the folding support means and to prevent any relative rotation between the implant and said folding device.

4. Packaging for folding intraocular implants according to claim 3, wherein the positioning means further comprise vertical retention means designed to prevent the edge of the optical portion of the implant from moving away from the base.

5. Packaging for folding intraocular implants according to claim 3, wherein the positioning means have respective shoulders forming means for retaining the intraocular implant radially.

6. Packaging for folding intraocular implants according to claim 1, wherein the positioning means comprise at least three point supports.

7. Packaging for folding intraocular implants according to claim 3, wherein at least some of the positioning means have an outline in a horizontal plane which is substantially identical to an outline of a corresponding zone of the periphery of the optical portion of the implant to be folded.

8. Packaging for folding intraocular implants according to claim 4, wherein the positioning means include at least one notch.

9. Packaging for folding intraocular implants according to claim 1, further including abutment means designed to limit the vertical stroke of a folding tool to be used therewith in a configuration suitable for holding the folded implant.

10. Packaging for folding intraocular implants according to claim 1, further including reference points enabling the implant to be positioned accurately relative to the folding device.

* * * * *